United States Patent
Ebel et al.

(10) Patent No.: US 6,495,729 B2
(45) Date of Patent: Dec. 17, 2002

(54) (+)- AND (−)-2-CYCLODODECYLPROPANOL AND (+)- AND (−)-2-CYCLODODECYLPROPIONIC ACID AND THE PREPARATION AND USE THEREOF

(75) Inventors: Klaus Ebel, Lampertheim (DE); Wolfgang Krause, Brühl (DE); Ulrich Schäfer-Lüderssen, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/847,301

(22) Filed: May 3, 2001

(65) Prior Publication Data

US 2002/0052306 A1 May 2, 2002

(30) Foreign Application Priority Data

May 12, 2000 (DE) .......................................... 100 23 256

(51) Int. Cl.[7] .......................... C07C 35/20; C07B 57/00; A61K 7/46
(52) U.S. Cl. ........................... 568/821; 562/401; 512/2; 512/8
(58) Field of Search ................... 512/2, 8, 26; 562/401; 568/821

(56) References Cited

U.S. PATENT DOCUMENTS 4,948,780 A * 8/1990 Hafner et al.

FOREIGN PATENT DOCUMENTS

| DE | 197 25 533 | 12/1998 |
|---|---|---|
| EP | 218 384 | 4/1987 |
| WO | WO 98/55228 | 12/1998 |
| WO | WO 98/56337 | 12/1998 |
| WO | WO 98/57914 | 12/1998 |
| WO | WO 99/31035 | 6/1999 |

OTHER PUBLICATIONS

Greve et al Angewandte Chemie International Edition in English 1996, 35(11), pp. 1221–1223.*

Theilacker "Methoden zur Herstellung optisch aktiver aus inaktiven Verbindungen" Allgemeine Chemische Methoden vol. 2 (1955) pp. 509–532.

Friedman et al. "Urea cycle enzyme adaptation to dietary protein in primates" Science vol. 172 No. 3986 (1971) pp. 1042–1046.

* cited by examiner

*Primary Examiner*—Paul J. Killos
*Assistant Examiner*—Paul A. Zucker
(74) *Attorney, Agent, or Firm*—Keil & Weinkauf

(57) ABSTRACT

The compounds are (+)- and (−)-2-cyclododecylpropanol and (+)- and (−)-2-cyclododecylpropionic acid, and salts thereof. (−)-2-cyclododecylpropanol is suitable as a fragrance while the virtually odorless (+) enantiomer is suitable as a fixative for other fragrances. The two enantiomers of 2-cyclododecylpropanol are prepared by reduction of the acid function of the enantiomers of 2-cyclododecylpropionic acid.

10 Claims, No Drawings

(+)- AND (−)-2-CYCLODODECYLPROPANOL AND (+)- AND (−)-2-CYCLODODECYLPROPIONIC ACID AND THE PREPARATION AND USE THEREOF (+)- and (−)-2-cyclododecylpropanol and (+)- and (−)-2-cyclododecylpropionic acid and the preparation and use thereof The present invention relates to (+)- and (−)-2-cyclododecylpropanol and (+)- and (−)-2-cyclododecylpropionic acid, to salts thereof, and to the preparation and use thereof.

The racemate of 2-cyclododecylpropanol (also called Hydroxyambran® or Amberwood®) is an odorant of the wood and ambergris class, which is becoming increasingly important (EP-B278 384). A process for its preparation, described in WO 98/55228, is the reaction of cyclodecene in the presence of catalytic amounts of a free-radical initiator with an excess of propionic acid or of a propionic acid derivative and subsequent catalytic hydrogenation of the resulting 2-cyclododecylpropionic acid or of the corresponding 2-cyclododecylpropionic acid derivative respectively.

Neither the two enantiomers of 2-cyclododecylpropionic acid nor of 2-cyclododecylpropanol have hitherto been disclosed in the prior art.

It is an object of the invention to prepare a fragrance of the wood and ambergris class which has a more intensive odor compared with the prior art and which is further notable for improved properties such as staying power, odor threshold value and a low limit of dilution.

We have found that this object is achieved according to the invention by (−)-2-cyclododecylpropanol.

Surprisingly, we have also found that while the (−)-enantiomer is highly suitable as a fragrance, the virtually odorless (+)-enantiomer is advantageously suitable as a fixative for other fragrances. It provides for a long-lasting adhesion, without adversely affecting the intrinsic odor of the adhering fragrance by a strong odor of its own.

The two enantiomers of 2-cyclododecylpropionic acid, the precursor and the intermediate for the preparation of cyclododecylpropanol are prepared by racemate resolution of known racemic 2-cyclododecylpropionic acid by crystallization of the diastereomeric salts using an optically active amine as auxiliary, and subsequent liberation of the respective enantiomer of the acid from the salt, e.g. by reaction with a strongly acidic ion exchanger. For further purification, the crystallization of the diastereomeric salt and the subsequent liberation of the acid can be carried out a number of times. Furthermore, the enantiomerically pure acid can be further purified by recrystallization (Houben-Weyl, Methoden der Organischen Chemie [Methods of Organic Chemistry], Volume IV, Allgemeine chemische Methoden, [General chemical methods], Part 2, Georg Thieme Verlag Stuttgart, 1955, pp. 505–532).

The two enantiomers of 2-cyclododecylpropanol are prepared by reduction of the acid function of the corresponding enantiomers of 2-cyclododecylpropionic acid. The reduction can be carried out, for example, by catalytic hydrogenation or using a complex hydride, for example lithium aluminum hydride.

The invention therefore also provides for the use of (+)- or (−)-2-cyclododecylpropionic acid as an intermediate for the preparation of (−)- or (+)-2-cyclododecylpropanol respectively Surprisingly, the odor of the enantiomers of 2-cyclododecylpropanol is completely different. While the (+)-enantiomer is virtually odorless, the (−)-enantiomer has a considerably stronger odor than the racemic mixture. The odor of racemic 2-cyclododecylpropanol is determined virtually exclusively by the (−)-enantiomer. Although it is known that enantiomers can differ in terms of odor (e.g. (+)-carvone [caraway], (−)-carvone [spearmint], L. Friedman, J. G. Miller, "Odor Incongruity and Chirality", Science 1971, 172, 1044, cited by G. Ohloff "Riechstoffe and Geruchsinn" [Odorants and sense of smell], p.42, Springer-Verlag 1990), the differences are usually qualitative in nature and only pronounced to a greater or lesser extent. The complete discrimination of the odor of the two enantiomers into highly odorous and odorless is extremely rare (cf. G. Ohloff "Riechstoffe and Geruchsinn", p.44, Springer-Verlag 1990) and has hitherto not been described for simple molecules having only one asymmetric center.

It is a particularly advantageous aspect for the use in perfume oils that the (−)-enantiomer is very compatible with all commercially available odorants, for example the classes of cyclic and acyclic terpenes, of aliphatic, cycloaliphatic, aromatic odorants, of phenol derivatives or of heterocycles.

EXAMPLES

Example 1

(−)-2-Cyclododecylpropionic Acid 215 g (0.85 mol) of racemic 2-cyclododecylpropionic acid with a purity of 95% were dissolved, at 50° C., in 250 ml of toluene and then 52.6 g (0.425 mol) of (R)-(+)-1-phenylethylamine were added. Then, also at 50° C., 430 ml of n-hexane were added, and the clear solution was left to cool. During this cooling, the salt precipitated out. After the mixture had been left to stand for three days at room temperature, the salt which had precipitated out was filtered off with suction and washed with n-hexane. Drying gave 85 g of the amine salt. The solution of this salt in 2.4 l of methanol was passed through a bed of 1 l of strongly acidic ion exchanger (Dowex 50 W×8) in a glass column 500 mm in height and 55 mm in diameter and then rinsed with methanol. The methanol was then stripped off on a rotary evaporator, giving 56 g of an oil which slowly began to crystallize. The residue was dissolved in 46 g of warm acetone. Upon cooling, 16 g of the acid (after washing with cold acetone and drying) crystallized with a content, according to GC on a chiral column, of 62% of (−)-2-cyclododecylpropionic acid and 38% of (+)-2-cyclododecylpropionic acid. Following concentration, the filtrate produced 42 g of a colorless oil with a content, according to GC on a chiral column, of 95% of (−)-2-cyclododecylpropionic acid and 5% of (+)-2-cyclododecylpropionic acid. This oil was dissolved in 246 ml of toluene at 50° C. and treated with 18.9 g of (R)-(+)-1-phenylethylamine. After cooling, 47 g (0.13 mol) of the amine salt crystallized out, which was filtered off with suction, washed with n-hexane and dried in the air. The dried amine salt was dissolved in 1.3 l of methanol, again freed from the amine over ion exchanger and the solution was then concentrated on a rotary evaporator, giving 30 g of a colorless oil, which slowly crystallized. The content of (−)-2-cyclododecylpropionic acid, determined by GC on a chiral column, was >98%.

Example 2

(+)-2-Cyclododecylpropionic Acid

The filtrate from the 1st crystallization of the amine salt from Example 1 was evaporated on a rotary evaporator, giving 222 g of an oil which was dissolved in 2200 ml of methanol and filtered. The filtered solution was then passed through a bed of 1 l of strongly acidic ion exchanger (Dowex 50 W×8) in a glass column 500 mm in height and 50 mm in diameter and then rinsed with methanol. The methanol was then stripped off on a rotary evaporator, giving 128 g of an oil which slowly began to crystallize. This oil was dissolved in 752 ml of toluene at 50° C. and treated with 42.4 g of (S)-(−)-1-phenylethylamine. After cooling, 92.5 g of the amine salt crystallized out, which was filtered off with suction, washed with n-hexane and dried in the air. The dried amine salt was dissolved in 2.5 l of methanol, again freed from the amine over ion exchanger, and the solution was then concentrated on a rotary evaporator, giving 55.5 g of a colorless oil with a content (GC on a chiral column) of 90% of (−)-2-cyclododecylpropionic acid and 10% of (+)-2-cyclododecylpropionic acid.

This oil was dissolved in 500 ml of toluene at 60° C. and treated with 24.5 g of (S)-(−)-1-phenylethylamine. After cooling, 65 g of the amine salt crystallized out, which was filtered off with suction, washed with n-hexane and dried in the air. The dried amine salt was dissolved in 1.8 l of methanol, again freed from the amine over ion exchanger, and the solution was then concentrated on a rotary evaporator, giving 43 g of a colorless oil with a content (GC on a chiral column) of >97% of (+)-2-cyclododecylpropionic acid.

Example 3

(+)-2-Cyclododecylpropanol 7 g of lithium aluminum hydride (0.183 mol) were introduced into 400 ml of anhydrous THF and, under a nitrogen atmosphere with gentle reflux, 30 g (0.125 mol of (−)-2-cyclododecylpropionic acid from Example 1 in 100 ml of anhydrous THF were added dropwise with stirring over the course of 3 h. The mixture was then refluxed for a further 4 h. Then, at room temperature, 12 ml of a 10% strength potassium hydroxide solution were added dropwise, and the mixture was refluxed for a further 15 min. The aluminum salts which had precipitated out were filtered off and washed with THF and then extracted twice more by boiling with 250 ml of THF in each case. The THF filtrates collected were concentrated on a rotary evaporator. The residue was taken up in 150 ml of toluene, washed with saturated sodium chloride solution and dried over sodium sulfate. Finally, the toluene was stripped off on a rotary evaporator, and the residue which remained was distilled, giving 24.2 g of a colorless oil with a purity of >97% of (+)-2-cyclododecylpropanol. The angle of rotation of 250 mg of this compound in 10 ml of abs. ethanol was +26.0 degrees. Odor characterization: very weak, virtually odorless Example 4

(−)-2-Cyclododecylpropanol 10 g of lithium aluminum hydride (0.264 mol) were introduced into 400 ml of anhydrous THF and, under a nitrogen atmosphere with gentle reflux, 43 g (0.179 mol) of (+)-2-cyclododecylpropionic acid from Example 2 in 130 ml of anhydrous THF were added dropwise with stirring over the course of 3 h. The mixture was then refluxed for a further 4 h. Then, at room temperature, 12 ml of a 10% strength potassium hydroxide solution were added dropwise, and the mixture was refluxed for a further 15 min. The aluminum salts which had precipitated out were filtered off and washed with THF and then extracted twice more by boiling with 250 ml of THF in each case. The THF filtrates collected were concentrated on a rotary evaporator. The residue was taken up in 150 ml of toluene, washed with saturated sodium chloride solution and dried over sodium sulfate. Finally, the toluene was stripped off on a rotary evaporator, and the residue which remained was distilled, giving 32 g of a colorless oil with a purity of >97% of (−)-2-cyclododecylpropanol. The angle of rotation of 250 mg of this compound in 10 ml of abs. ethanol was =25.2 degrees.

Odor characterization:

Odor character: strongly ambergris-like/woody with dominating ambergris character and linear scent development Intensity: very strong, significantly stronger than racemic product Scent Adhesion (10% strength solution in ethanol): >1 month (+)-Enantiomer:

Woody-linear, no significant scent facets, adhesion greater than 1 month

We claim:

1. A 2-cyclododecylpropanol which has a content of (+)-2-cyclododecylpropanol of >97%, or a derivative or ester thereof.

2. A 2-cyclododecylpropanol which has a content of (−)-2-cyclododecylpropanol of >97%, or a derivative or ester thereof.

3. A 2-cyclododecylpropionic acid which has a content of (+)-2-cyclododecylpropionic acid of >97%, or a salt thereof.

4. A 2-cyclododecylpropionic acid which has a content of (−)-2-cyclododecylpropionic acid of >98%, or a salt thereof.

5. A perfume oil mixture comprising 2-cyclododecylpropanol or a derivative or ester thereof as a component, wherein the 2-cyclododecylpropanol has a content of (+)-2-cyclododecylpropanol of >97%.

6. A fragrance composition comprising 2-cyclodode- cylpropanol or a derivative or ester thereof, wherein the 2-cyclododecylpropanol has a content of (−)-2-cyclododecyl-propanol of >97%.

7. A process for the preparation of the 2-cyclodode-cylpropanol defined in claim 2, which comprises separating racemic 2-cyclododecylpropionic acid into
a) a (+)-2-cyclododecylpropionic acid having a purity of >97%, and
b) a (−)-2-cyclododecylpropionic acid having a purity of >98%,
and subsequently reducing the (+)-2-cyclododecylpropionic acid.

8. A process for the preparation of the 2-cyclododecyl-propanol defined in claim 1, which comprises separating racemic 2-cyclododecylpropionic acid into
a) a (+)-2-cyclododecylpropionic acid having a purity of >97%, and
b) a (−)-2-cyclododecylpropionic acid having a purity of >98%,
and subsequently reducing the (−)-2-cyclododecylpropionic acid.

9. A 2-cyclododecylpropanol which has a content of (+)-2-cyclododecylpropanol of >97%.

10. A 2-cyclododecylpropanol which has a content of (−)-2-cyclododecylpropanol of >97%.

* * * * *